United States Patent [19]

Morita et al.

[11] Patent Number: 5,071,751

[45] Date of Patent: Dec. 10, 1991

[54] PROCESS FOR PREPARING HYALURONIC ACID

[75] Inventors: Hiroshi Morita, Yokohamashi; Masahiro Fujii, Tokyoto, both of Japan

[73] Assignee: Chisso Corporation, Osaka, Japan

[21] Appl. No.: 336,913

[22] Filed: Apr. 12, 1989

Related U.S. Application Data

[63] Continuation-in-part of Ser. No. 772,422, Sep. 4, 1985, abandoned.

[30] Foreign Application Priority Data

Sep. 4, 1984 [JP] Japan .............................. 59-185150
Apr. 16, 1985 [JP] Japan .............................. 60-80949

[51] Int. Cl.$^5$ .................... C12P 19/04; C12N 1/38; C12N 1/00; C08B 37/00
[52] U.S. Cl. ............................ 435/101; 435/252.1; 435/244; 536/55.1
[58] Field of Search ............... 435/101, 315, 885, 244, 435/84, 252.1; 536/123, 55.1

[56] References Cited

U.S. PATENT DOCUMENTS

| 3,063,914 | 11/1962 | von Polnitz | 435/885 |
| 3,929,571 | 12/1975 | Kubota | 435/115 |
| 3,988,205 | 10/1976 | Boguth | 435/885 |

FOREIGN PATENT DOCUMENTS

| 1063293 | 4/1986 | Japan | 435/101 |
| 1239898 | 10/1986 | Japan | 435/101 |

OTHER PUBLICATIONS

Buchanan et al., *Veterinary Microbiology*, vol. 7, pp. 19–33, 1982.

"Bergeys Manual of Determinative Microbiology", 1984, p. 498.

*Primary Examiner*—Douglas W. Robinson
*Assistant Examiner*—Irene Marx
*Attorney, Agent, or Firm*—Fred Philpitt

[57] ABSTRACT

A process for producing a hyaluronic acid can be provided steadly, with a greatly improved productivity and at an inexpensive cost by incubating a hyaluronic acid-producing microbe in a culture medium formed by adding a blood serum or a bacteriolytic enzyme and/or a surfactant, accumulating and isolating the hyaluronic acid.

2 Claims, No Drawings

PROCESS FOR PREPARING HYALURONIC ACID

RELATED APPLICATION

This application is a continuation-in-part of Ser. No. 772,422, filed Sept. 4, 1985, now abandoned, and the benefits of 35 USC 120 are claimed relative to it.

BACKGROUND OF THE INVENTION

Field of the Invention and Related Art Statement

The present invention relates to a process for preparing hyaluronic acid with a microbe capable of producing hyaluronic acid (hereinafter referred to as a "hyaluronic acid-producing microbe"). More specifically, this invention relates to a process for preparing hyaluronic acid comprising incubating a hyaluronic acid-producing microbe in a culture medium containing blood serum, a bacteriolytic enzyme, a surface active agent, or a bacteriolytic enzyme plus a surface active agent to yield and accumulate hyaluronic acid in the culture medium, and isolating the same.

Hyaluronic acid exists in connective tissues such as joints, vitreous bodies, umbilical cords, cartilages, skins, and combs of fowls as a constituent thereof, and fulfils important functions such as flexibility and structure maintainence of tissues, and metabolic regulation of cells. Hyaluronic acid is a very large high molecular weight polymer, and a solution thereof has a high viscoelasticity and a water-holding function. Therefore, it has a wide variety of uses in cosmetics, medicines for wounds, eye waters, medicines for arthritis.

Hyaluronic acid has heretofore been commercially obtained by a method of extraction thereof from combs of fowls, vitreous bodies of bovine eyes, umbilical cords, cetacean cartilages, or the like. However, hyaluronic acid obtained from living bodies by the extraction method is in the form of a complex formed with a protein or a mucopolysaccharide such as chondroitin, and hence, needs complicated steps for separation and purification. Furthermore, since it is present in most cases in the form of a mixture with hyaluronidase, there has been drawbacks in that such a hyaluronic acid may be decomposed in the course of extraction and purification steps to reduce its molecular weight, and as consequent effects thereof its viscosity and water-holding property are lowered. In view of the above, an attempt to prepare hyaluronic acid by the cultivation method has been disclosed in Japanese Patent Laid-Open Specification No. 56692/1983. However, it is a difficult point of this method that the productivity of hyaluronic acid is poor.

The inventors of the present invention have made intensive investigations in order to solve the above-mentioned problem involved in the preparation of hyaluronic acid. As a result, it has been found that use of a culture medium containing blood serum added thereto or a culture medium containing a bacteriolytic enzyme and/or a surface active agent added thereto in incubation of a hyaluronic acid-producing microbe largely increases the productivity of hyaluronic acid. The present invention has been completed based on this finding.

THE OBJECT AND SUMMARY OF THE INVENTION

As is apparent from the foregoing description, the object of this invention is to provide a process for preparing hyaluronic acid with a stable and greatly increased productivity and at a low cost.

In one aspect of the present invention, there is provided a process for preparing hyaluronic acid comprising the steps of incubating a microbe capable of producing hyaluronic acid in a culture medium containing blood serum added thereto to yield and accumulate hyaluronic acid in the culture medium, and isolating hyaluronic acid therefrom.

In another aspect of the present invention, there is provided a process for preparing hyaluronic acid comprising the steps of incubating a microbe capable of producing hyaluronic acid in a culture medium containing a bacteriolytic enzyme and/or a surface active agent added thereto to yield and accumulate hyaluronic acid in the culture medium, and isolating hyaluronic acid therefrom.

DETAILED DESCRIPTION OF THE INVENTION

As the hyaluronic acid-producing microbe to be used in the process of this invention, there can be mentioned, for example, *Streptococcus equi* Ferm BP-879, *Streptococcus zooepidemicus*, Ferm BP-878.

In the process of this invention, there may be used any one of bovine blood serum, equine blood serum, swine's blood serum, caprine blood serum, sheep's blood serum, fowl's blood serum, and human blood serum. As to bovine blood serum, there may be used blood serum taken from any one of a fetus, a new-born calf, a calf, a cow, and a bull. In place of blood serum, whole blood taken from a bovine, an equine, a swine, a goat, a sheep, a fowl, or a human being may be used. Alternatively, a component differentiated from blood serum of any animal as mentioned above or a human being may be used in place of blood serum and the component fractionated from blood serum containing lysozyme. The amount of blood serum to be added to the culture medium is preferably 0.3%-5.0% by volume, most preferably 1.5% by volume.

As the bacteriolytic enzyme that may be used in the process of this invention, all bacteriolysis-active enzymes are usable, but lysozyme is most preferred. The amount of the bacteriolytic enzyme that may be added to the culture medium is not particularly limited but is preferably 100 to 2,500 units, more preferably 300 to 2,000 units, most preferably 500 to 1,000 units, per liter of the culture medium. Too small an amount of the bacteriolytic enzyme added results in a small amount of hyaluronic acid yielded and accumulated. Too large an amount of the bacteriolytic enzyme added disadvantageously leads to so much bacteriolysis that the growth of the hyaluronic acid-producing microbe may be obstructed.

As to the timing of addition of the bacteriolytic enzyme to the culture medium, it is preferred to make the addition under aseptic conditions after sterilization of a culture medium to which the enzyme is to be added, for example, according to the pressure steam sterilization method, and subsequent cooling to a temperature of 45° C. or lower.

Examples of the surface active agent that may be used in the process of this invention include cetyltrimethylammonium bromide, cetylpyridinium chloride, Tween 80 (trade name of a surfactant manufactured by Kao Kagaku Kabushiki Kaisha), Tween 90 (trade name of a surfactant manufactured by Kao Kagaku Kabushiki Kaisha), sodium laurylsulfate, Triton X-100 (trade name of a surfactant manufactured by Rohm & Haas Co.), Span 80 (trade name of a surfactant manufactured by Kao Kagaku Kabushiki Kaisha), Span 90 (trade name of a surfactant manufactured by Kao Kagaku Kabushiki Kaisha), Nonion(trade name of a surfactant manufactured by Nippon Oil and Fats Co., Ltd, and diethyhexyl sulfosuccinate. The amount of the surface active agent to be added to the culture medium is preferably 0.5 to 10 g, more preferably 0.5 to 3 g, most preferably 1.0 to 2.0 g, per liter of the culture medium. The surface active agent is added to the culture medium before sterilization of the culture medium with pressure steam.

In the process of the present invention, a culture medium before addition of the blood serum, or the bacteriolytic enzyme and/or the surface active agent may be any usually employed culture medium for incubating a hyarulonic acid-producing microbe, and may contain, for example, 2.0 to 3.0% of glucose, 0.5% of a yeast extract, 1.5% of peptone, 0.3% of potassium dihydrogenphosphate, 0.2% of potassium monohydrogenphosphate, 0.01% of sodium thiosulfate, 0.01% of magnesium sulfate heptahydrate, 0.002% of sodium sulfite, 0.001% of cobalt (II) chloride, 0.001% of manganese (II) chloride, and a 0.5% of a defoaming agent and may have a pH of, for example, 6.0 to 8.5 or 2.0% of glucose, 0.3% of potassium dihydrogen-phosphate, 0.2% of potassium monohydrogenphosphate, 0.01% of sodium thiosulfate, 0.01% of magnesium sulfate heptahydrate, 0.002% of sodium sulfite, and 0.5% of a defoaming agent and may have a pH of, for example, 6.0 to 8.5. (Every % herein and hereinafter mentioned means a weight/volume % wherein the weight and the volume are expressed in terms of gram and deciliter, respectively unless otherwise described.)

In the process for preparing hyaluronic acid according to the present invention, a culture medium containing no blood serum is sterilized, for example, according to the pressure steam sterilization method, and cooled to a temperature of 45° C. or lower, at which blood serum may be added to the above-mentioned culture medium under aseptic conditions. Subsequently, a hyaluronic acid-preparing microbe is inoculated into the resulting culture medium. The culture medium is then agitated by blowing air therethrough or allowed to stand at a temperature of preferably 25° C. to 40° C., particularly preferably 35° C., and at a controlled pH of preferably 6.5 to 8.0, most preferably about 7.0, for 1 to 2 days to effect incubation, followed by further addition of a saccharide component in an amount of 3% to the culture medium and further incubation for 10 hours to 2 days to yield and accumulate hyaluronic acid.

Alternatively, a culture medium containing neither an bacteriolytic enzyme nor a surface active agent or a culture medium containing a surface active agent and no bacteriolytic enzyme is sterilized, for example, according to the pressure steam sterilization method, and cooled to a temperature of 45° C. or lower, at which an bacteriolytic enzyme is added to the culture medium under aseptic conditions, followed by inoculation of a hyaluronic acid-producing microbe into the resulting culture medium under aseptic conditions. Where no bacteriolytic enzyme is to be added, a culture medium containing a surface active agent added thereto is sterilized, for example, according to the above-mentioned pressure steam sterilization method, and cooled to a temperature of 45° C. or lower, at which a hyaluronic acid-producing microbe is inoculated into the culture medium under aseptic conditions. The culture medium is then agitated under an air stream blowing or allowed to stand at a temperature of preferably 25° C. to 40° C., particularly preferably 30° C. to 35° C., and at a controlled pH of preferably 6.5 to 8.0, most preferably 7.0, for 1 to 2 days to effect incubation, followed by further addition of a saccharide component in an amount of 3% to the culture medium and further incubation for 1 to 2 days to yield and accumulate hyaluronic acid.

Thereafter, the culture medium is rid of the microbe by centrifugal separation or filtration, and the resulting filtrate is stripped of low molecular weight substances by ultrafiltration or dialysis. Subsequently, an alcohol such as methanol or ethanol may be added to the filtrate stripped of the low molecular weight substances to precipitate a crude product of hyaluronic acid. The precipitated hyaluronic acid is dissolved in water again. Thereafter, cetyltrimethylammonium bromide is added to the resulting solution to effect differential precipitation with the cetyltrimethylammonium bromide. Subsequently, a known purification procedure such as ion exchange chromatography or gel permeation chromatography is applied to purify the resulting hyaluronic acid.

By using a culture medium containing blood serum added thereto or a culture medium containing a bacteriolytic enzyme and/or a surface active agent added thereto according to the process of the present invention, the productivity of hyaluronic acid can be greatly improved e.g. by 4 to 5 times, per liter of the culture medium, as compared with that of the method of incubation carried out by using an ordinary culture medium containing none of blood serum, an bacteriolytic enzyme, and a surface active agent (see Comparison Examples). Furthermore, since there is almost no lot-to-lot variation in quality of the bacteriolytic enzyme and the surface active agent to be used, hyaluronic acid can be always prepared with a constant quality and productivity. Thus the present invention provides an epoch-making process for preparing hyaluronic acid. The content of the impurities in the hyaluronic acid obtained according to the process of this invention is so exceedingly small that the product of the process of the present invention is the highest grade of hyaluronic acid. Thus it can be favorably employed in applications to pharmaceuticals and cosmetics.

As has hereinbefore be described, it was confirmed that the process for preparing hyaluronic acid according to the present invention is a process capable of producing high purity hyaluronic acid in a stabilized manner with a high productivity.

The following Examples will specifically illustrate the present invention in contradictinction to Comparison Examples, but should not be construed as limiting the scope of the invention.

*Streptococcus equi* Ferm BP-879 and *Streptococcus zooepidemicus* Ferm BP 878 used in the present invention have been deposited under the Budapest Treaty and will be irrevocably and without restriction or condition released to the public upon the issuance of a patent.

EXAMPLE 1 AND COMPARISON EXAMPLE 1

22.5 ml of blood serum of a bovine new-born was added under aseptic conditions to 1.5 liters of a culture medium containing 2.0% of glucose, 0.3% of potassium dihydrogenphosphate, 0.2% of potassium monohydrogenphosphate, 0.011% of sodium thiosulfate, 0.01% of magnesium sulfate heptahydrate, 0.002% of sodium sulfite, 0.001% of cobalt (II) chloride, 0.001% of manganese (II) chloride, and 1.0% of soybean 091, and having a pH of 7.0. 100 ml of a previously prepared culture medium of *Streptococcus equi* Ferm BP-879 was inoculated into the resultant culture medium, and the microbe was incubated under an air stream of 0.7 vvm at a rotation of a stirrer of 300 rpm at a temeprature of 35° C. for 40 hours while automatically controlling the pH to 7.0. Thereafter, 25 g of glucose was added to the culture medium under aseptic conditions, followed by further incubation for 10 hours. 1.6 liters of ion-exchanged water was then added to the resulting culture medium, followed by centrifugal separation to remove the microbe. Dilute hydrochloric acid was added to the supernatant thus obtained to adjust the pH thereof to 5.5. The resulting solution was concentrated by a hollow-fiber ultrafilter to 0.75 liter, and dialyzed against ion-exchanged water. The resulting solution was purified by known methods; successively by differential precipitation with ethyl alcohol, treatment with cetylpyridinylammonium chloride, and chromatography with ion-exchange Cellulofine (trade mark) to obtain 8.7 g of a white powder of purified sodium Hyalurouate.

The amount of the product was 5.8 g per liter of the culture medium. The protein content of the purified sodium hyaluronate was 0.05% by weight. The molecular weight of the purified sodium hyaluronate was measured by gel permeation chromatography with Sepharose 6B (trade name) manufactured by Pharmcia Finechemicals Co., and found to be $2 \times 10^6$ daltons. A physiological saline containing 1% by weight of the sodium hyaluronate was intravenously injected to a rabbit, which, however, did not show any pyrogeneous reaction.

In a run as Comparison Example 1, a hyaluronic acid-producing microbe was incubated under the same conditions and in the same procedure as in Example 1 except that a culture medium in which serum component was removed from and 0.5% of a yeast extract and 1.5% of peptone were added to the culture medium of Example 1 was used. The resultant culture medium was subjected to the same treatment and purification as in Example 1 to obtain 0.9 g of a white powder of purified sodium hyaluronate. The amount of the product was 0.6 g per liter of the culture medium.

EXAMPLE 2

1.5 liters of a culture medium containing 2.0% of glucose, 0.5% of a yeast extract, 1.5% of peptone, 0.3% of potassium dihydrogenphosphate, 0.2% of potassium monohydrogenphosphate, 0.011% of sodium thiosulfate, 0.01% of magnesium sulfate heptahydrate, 0.002% of sodium sulfite, 0.001% of cobalt (II) chloride, 0.001% of manganese (II) chloride, and 0.5% of soybean oil, and having a pH of 7.0 was poured into a minijar fermentor having an internal volume of 3.0 liters, and sterilized with pressure steam at 120° C. for 15 minutes, followed by cooling to room temperature. 0.75 mg (675 units) of egg albumen lysozyme was added to the resultant culture medium under aseptic conditions. Subsequently, 0.1 leter of a previously prepared culture medium of *Streptococcus zooepidemicus* Ferm BP-878 was inoculated into the culture medium, and the microbe was incubated under an air stream of 0.7 vvm at a rotation of a stirrer of 300 rpm at 35° C. for 24 hours while automatically adjusting the pH to 7.0. Thereafter, 100 ml of a 50% aqueous glucose solution was added to the culture medium under aseptic conditions. Incubation was further continued under the above-mentioned incubation conditions for 26 hours. 3.2 liters of ion-exchanged water was added to the resultant culture medium, followed by agitation and centrifugal separation for removal of the microbe. The supernatant thus obtained was concentrated to 1.6 liters by a hollow-fiber ultrafilter, and dialyzed against ion-exchanged water. Sodium acetate was added to the resulting solution so as to give a sodium acetate content of 0.5%, followed by addition of 5 liters of ethanol for precipitation of polysaccharides including hyaluronic acid which is thereafter isolated by centrifugal separation.

The isolated polysaccharides containing hyaluronic acid was dissolved in 0.5 liter of ion-exchanged water, and 0.23 liter of a 4% of aqueous cetyltrimethylammonium bromide solution was added to the resulting solution, followed by separation of a precipitate formed. The precipitate was dispersed in 40 ml of an aqueous sodium chloride solution having a concentration of 0.3 mole/liter, followed by centrifugal separation. 120 ml of ethanol was added to the supernatant solution, followed by separation of a precipitate formed. The precipitate was dissolved in ion-exchanged water, and purified by ion exchange chromatography to obtain 7.8 g of a white powder of purified sodium hyaluronate. The amount of the product was 5.2 g per liter of the culture medium. The purified sodium hyaluronate had a protein content of 0.05% by weight. The intrinsic viscosity [$\eta$] of the purified sodium hyaluronate as measured by an Ubbellohde viscometer was 17.3 dl/g. Thus it was confirmed that the molecular weight thereof was 1,005,000 daltons.

EXAMPLE 3

1.5 liters of a culture medium containing 2.0% of glucose, 0.5% of a yeast extract, 1.5% of peptone, 0.3% of potassium dihydrogenphosphate, 0.2% of potassium monohydrogenphosphate, 0.011% of sodium thiosulfate, 0.01% of magnesium sulfate heptahydrate, 0.002% of sodium sulfite, 0.001% of cobolt (II) chloride 0.001% of manganese (II) chloride, 0.5% of soybean oil, and 1.5 g of Tween 80 (trade name) as the surface active agent, and having a pH of 7.0 was poured into a minijar fermentor having an internal volume of 3.0 liters, and sterilized with pressure steam at 120° C. for 15 minutes, followed by cooling to room temperature. Subsequently, 0.1 liter of a previously prepared culture medium of *Streptococcus equi* Ferm BP-879 was inoculated into the resulting culture medium under aseptic conditions, and the microbe was incubated under the same incubation conditions and by the same incubation method as in Example 2. Thereafter, the culture medium was subjected to the same purification treatment as in Example 2 to obtain 6.1 g of a white powder of sodium hyaluronate. The amount of the product was 4.1 g per 1 liter of the culture medium. The purified sodium hyaluronate had a protein content of 0.03% by weight. The intrinsic viscosity [$\eta$] thereof as measured by an Ubbellohde viscometer was 12.0 dl/g. Thus it was confirmed that the molecular weight thereof was 628,000 daltons.

EXAMPLE 4

0.7 g of Tween 80 (trade name) as the surface active agent was added to 1.5 liters of a culture medium containing 2.0% of glucose, 0.5% of a yeast extract, 1.5% of peptone, 0.3% of potassium dihydrogenphosphate, 0.2% of potassium monohydrogenphosphate, 0.011% of sodium thiosulfate, 0.01% of magnesium sulfate heptahydrate, 0.002% of sodium sulfite, 0.001% of cobolt (II) chroride, 0.00% of manganese (II) chroride, and 0.5% of soybean oil, and having a pH of 7.0. The culture medium was then poured into a minijar fermentor having an internal volume of 3.0 liters, and sterilized with pressure steam at 120° C. for 15 minutes, followed by cooling to room temperature. 0.4 mg (360 units) of egg albumen lysozyme was then added to the culture medium under aseptic condition. Subsequently, 0.1 liter of a previously prepared culture medium of *Streptococcus zooepidemicus* Ferm BP-878 was inoculated into the culture medium, and the microbe was incubated under the same incubation conditions and by the same incubation method as in Example 2. Thereafter, the resultant culture medium was subjected to the same purification treatment as in Example 2 to obtain 8.0 g of a white powder of purified sodium hyaluronate. The amount of the product was 5.3 g per liter of the culture medium. The purified sodium hyaluronate had a protein content of 0.04% by weight. The intrinsic viscosity [η] thereof as measured by an Ubbellohde viscometer was 15.0 dl/g. Thus it was confirmed that the molecular weight thereof was 837,000 daltons.

COMPARISON EXAMPLE 2

1.5 liters of a culture medium containing 2.0% of glucose, 0.5% of a yeast extract, 1.5% of peptone, 0.3% of potassium dihydrogenphosphate, 0.2% of potassium monohydrogenphosphate, 0.011% of sodium thiosulfate, 0.01% of magnesium sulfate heptahydrate, 0.002% of sodium sulfite, 0.001% of cobolt (II) chroride, 0.00% of manganese (II) chroride, and 0.5% of soybean oil, and having a pH of 7.0 was poured into a minijar fermentor having an internal volume of 3.0 liters, and sterilized with pressure steam at 120° C. for 15 minutes followed by cooling to room temperature. Subsequently, 0.1 liter of a previously prepared culture medium of *Streptococcus zooepidemicus* Ferm BP-878 was inoculated into the culture medium, and the microbe was incubated under the same incubation conditions and by the same incubation method as in Example 2. Thereafter, the culture medium was subjected to the same purification treatment as in Example 2 to obtain 1.5 g of a white powder of purified sodium hyaluronate. The amount of the product was 1.0 g per liter of the culture medium. The purified sodium hyaluronate had a protein content of 0.03% by weight. The intrinsic viscosity [η] thereof as measured by an Ubbellohde viscometer was 12.0 dl/g. Thus it was confirmed that the molecular weight thereof was 628,000 daltons.

EXAMPLES 5-7 AND COMPARATIVE EXAMPLE 3

In Example 5, to the same amount of and the same kind of the culture medium as used in Example 1, the same amount of *Streptococcus equi* FERM BP-879 as used in Example 1 was added and under the condition based upon Example 1, incubation was carried out for 11 hours.

In Example 6, to the same amount of and the same kind of the culture medium as used in Example 2, the same amount of *Streptococcus zooepidemicus* FERM BP-878 as used in Example 2 was added and under the condition based upon Example 2, incubation was carried out for 11 hours.

In Example 7, to the same amount of and the same kind of the culture medium as used in Example 3, the same amount of *Streptococcus equi* FERM BP-879 as used in Example 3 was added and under the condition based upon Example 3, incubation was carried out for 11 hours.

In comparative Example 3, to the same amount of and the same kind of the culture medium as used in Comparative Example 1, the same amount of *Streptococcus equi* FERM BP-879 as used in Comparative Example 1 was added under the condition based upon Comparative Example 1, incubation was carried out for 11 hours.

10 ml of each of the culture mediums obtained in Examples 5 to 7 and Comparative Example 3, respectively, were taken up and radia of formed capsules were measured by using an optical microscope. With regard to the remaining other culture mediums, purification treatments were carried out in Example 5 by the procedure based upon Example 1, in Example 6 by the procedure based upon Example 2, in Example 7 by the procedure based upon Example 3, in Comparative Example 3 by the procedure based upon Comparative Example 1, respectively and purified sodium hyaluronate were obtained.

The results of these experiments are shown in Table 1.

TABLE 1

| | additives | radia (μm) of capsule | | number of measurement | production amount of hyaluronic acid (g) per 1 L of culture medium |
| --- | --- | --- | --- | --- | --- |
| | | mean value | standard deviation | | |
| Example 5 | blood serum | 1.88 | ±0.390 | 26 | 6.0 |
| Example 6 | Lysozyme | 2.17 | ±0.334 | 18 | 5.5 |
| Example 7 | Tween 80 | 1.71 | ±0.245 | 22 | 4.5 |
| comparative example 3 | none | 2.52 | ±0.455 | 14 | 0.7 |

When these results are subjected to test, significant differences are recognized at 99% reliability between Examples 5 or 7 and Comparative Example 3, and at 90% reliability between Example 6 and Comparative Example 3. Thus, it can be seen that the formation of capsule becomes less by the addition of blood serum, Lysozyme or Tween 80. This means that the above-mentioned additives suppress the accumulation to the hyaluronic acid capsule and performs the function of liberating hyaluronic acid to the culture medium.

What we claim is:

1. A process for preparing hyaluronic acid comprising the steps of incubating a microbe capable of producing hyaluronic acid selected from the group consisting of *Streptococcus equi* FERM BP-879 and *Streptococcus zooepidemicus* FERM BP-878 in a culture medium containing newborn bovine blood serum added thereto, agitating the resultant culture medium by passing an air stream therethrough for effecting incubation while controlling the incubation temperature at 25° C. to 40° C. and at pH of 6.5 to 8.0, accumulating the resultant hyaluronic acid in said culture medium, and isolating hyaluronic acid therefrom.

2. A process for preparing hyaluronic acid comprising the steps of incubating a microbe capable of producing hyaluronic acid selected from the group consisting of *Streptococcus equi* FERM BP-879 and *Streptococcus zooepidemicus* FERM BP-878 in a culture medium containing at least one member selected from the group consisting of a lysozyme and a surface active agent added thereto, agitating the resultant culture medium by passing an air stream therethrough for effecting incubation while controlling the incubation temperature at 25° C. to 40° C. and a pH of 6.5 to 8.0, accumulating the resultant hyaluronic acid in said culture medium, and isolating hyaluronic acid therefrom.

* * * * *